United States Patent
Christensen et al.

(10) Patent No.: US 10,214,404 B2
(45) Date of Patent: Feb. 26, 2019

(54) TEST TUBE CAPPING AND DE-CAPPING APPARATUS

(71) Applicant: Cedrex A/S, Karlslunde (DK)

(72) Inventors: Stig Christensen, Greve (DK); Lars Hovendahl, Hvalsø (DK); Michael Gabs Kaagaard Nielsen, Lejre (DK)

(73) Assignee: Cedrex A/S, Karlslunde (DK)

( * ) Notice: Subject to any disclaimer, the term of this patent is extended or adjusted under 35 U.S.C. 154(b) by 1009 days.

(21) Appl. No.: 14/419,854

(22) PCT Filed: Aug. 5, 2013

(86) PCT No.: PCT/EP2013/066365
§ 371 (c)(1),
(2) Date: Feb. 5, 2015

(87) PCT Pub. No.: WO2014/023683
PCT Pub. Date: Feb. 13, 2014

(65) Prior Publication Data
US 2015/0175398 A1 Jun. 25, 2015

(30) Foreign Application Priority Data
Aug. 7, 2012 (DK) .................................. 2012 00492

(51) Int. Cl.
*B67B 3/20* (2006.01)
*G01N 35/04* (2006.01)
(Continued)

(52) U.S. Cl.
CPC .............. *B67B 3/2066* (2013.01); *B67B 3/20* (2013.01); *B67B 3/2073* (2013.01); *B67B 7/182* (2013.01);
(Continued)

(58) Field of Classification Search
CPC ....... B67B 3/2066; B67B 3/2073; B67B 3/20; B67B 7/182; B67B 1/06; B67B 7/18;
(Continued)

(56) References Cited

U.S. PATENT DOCUMENTS 2,559,358 A * 7/1951 Hullhorst .............. B67B 3/2053
192/61
3,589,103 A * 6/1971 Calvillo ................ B67B 3/2053
53/381.4
(Continued)

FOREIGN PATENT DOCUMENTS

EP 1424307 6/2004
EP 1659091 5/2006
(Continued)

OTHER PUBLICATIONS

International Search Report, PCT/EP2013/066365, dated Feb. 21, 2014.
(Continued)

*Primary Examiner* — Alexander Valvis
*Assistant Examiner* — Mobeen Ahmed
(74) *Attorney, Agent, or Firm* — Hamilton, Brook, Smith & Reynolds, P.C.

(57) ABSTRACT

An apparatus (100) for automated capping and de-capping of test tubes (112) having an ejector pin (230) system for individualized cap (113) ejection.

15 Claims, 5 Drawing Sheets

(51) Int. Cl.
  *B67B 7/18* (2006.01)
  *B65B 7/28* (2006.01)
  *B67B 1/06* (2006.01)

(52) U.S. Cl.
  CPC .......... *G01N 35/04* (2013.01); *B65B 7/2828* (2013.01); *B65B 7/2835* (2013.01); *B67B 1/06* (2013.01); *B67B 7/18* (2013.01); *G01N 2035/0405* (2013.01); *G01N 2035/0418* (2013.01)

(58) Field of Classification Search
  CPC ............... B67B 2007/18; G01N 35/04; G01N 2035/0418; G01N 2035/0405; B65B 7/2835; B65B 7/2828
  USPC ............ 53/299, 317, 331.5, 490, 318.4, 492
  See application file for complete search history.

(56) References Cited

U.S. PATENT DOCUMENTS

| | | | | |
|---|---|---|---|---|
| 3,683,598 A * | 8/1972 | Van Zijp | | B67B 3/2073 53/317 |
| 3,775,829 A * | 12/1973 | Rice | | B67B 7/182 29/426.3 |
| 3,803,795 A * | 4/1974 | Ouellette | | B67B 7/182 53/381.4 |
| 3,852,941 A * | 12/1974 | Bross | | B65B 7/2835 53/317 |
| 4,265,071 A * | 5/1981 | Smith | | B67B 7/182 53/331.5 |
| 4,357,787 A * | 11/1982 | Long | | B67B 3/2073 53/272 |
| 4,519,276 A * | 5/1985 | Grabarski | | B67B 7/182 81/3.09 |
| 4,616,466 A * | 10/1986 | Tanaka | | B67B 3/2033 53/317 |
| 4,906,147 A * | 3/1990 | Friesinger | | B23B 31/113 279/97 |
| 4,934,040 A * | 6/1990 | Turchan | | B23G 1/32 29/566 |
| 5,301,488 A * | 4/1994 | Ruhl | | B67C 7/00 53/282 |
| 5,321,935 A * | 6/1994 | Spatz | | B67B 3/208 53/317 |
| 5,327,697 A * | 7/1994 | Kent | | B67B 3/2073 53/331.5 |
| 5,687,552 A * | 11/1997 | Barca | | B67B 3/206 53/306 |
| 5,718,097 A * | 2/1998 | Kinoshita | | G01N 1/286 53/201 |
| 5,884,450 A * | 3/1999 | Ronchi | | B67B 3/00 53/281 |
| 6,158,196 A * | 12/2000 | Trebbi | | B67B 3/2033 53/317 |
| 6,170,232 B1 * | 1/2001 | VandeGeijn | | B23B 31/113 279/4.09 |
| 6,216,340 B1 * | 4/2001 | Fassbind | | B67B 7/182 29/773 |
| 6,240,678 B1 * | 6/2001 | Spether | | B67B 3/2073 53/317 |
| 6,508,046 B1 * | 1/2003 | Resterhouse | | B67B 3/2066 53/331.5 |
| 7,024,837 B2 * | 4/2006 | Takebe | | B67B 3/20 53/317 |
| 7,647,746 B2 * | 1/2010 | Ueda | | B67B 3/18 53/317 |
| 7,661,245 B2 * | 2/2010 | Brown | | B67B 3/2066 53/317 |
| 7,874,127 B2 * | 1/2011 | Brown | | B67B 3/2066 53/317 |
| 8,166,730 B2 * | 5/2012 | Schmatz | | B67B 3/2066 53/317 |
| 8,915,047 B2 * | 12/2014 | Wilhelm | | B67B 3/12 53/287 |
| 9,381,524 B2 * | 7/2016 | Bailey | | B04B 11/043 |
| 2001/0026135 A1 * | 10/2001 | Zalkin | | B67B 3/208 318/432 |
| 2002/0184853 A1 * | 12/2002 | Arrant | | B65B 7/2835 53/343 |
| 2003/0175156 A1 * | 9/2003 | Ford | | B01L 3/04 422/63 |
| 2004/0065049 A1 * | 4/2004 | Cirio | | B67B 3/2033 53/317 |
| 2004/0139811 A1 * | 7/2004 | Cirio | | B67B 3/2033 73/865.9 |
| 2005/0144908 A1 * | 7/2005 | Yang | | B65B 7/2835 53/331.5 |
| 2005/0183388 A1 * | 8/2005 | Cirio | | B67B 3/2033 53/287 |
| 2006/0130597 A1 * | 6/2006 | Bernard | | B01L 9/06 73/864.21 |
| 2008/0022808 A1 * | 1/2008 | Owen | | G01N 35/026 81/3.2 |
| 2009/0293437 A1 * | 12/2009 | Schulz | | B67B 3/2033 53/490 |
| 2011/0083405 A1 * | 4/2011 | Dewert | | B67B 3/20 53/490 |
| 2011/0289889 A1 * | 12/2011 | Kohanski | | B01L 3/50853 53/485 |
| 2013/0239522 A1 * | 9/2013 | Melrose | | B65D 1/0223 53/467 |
| 2014/0174028 A1 * | 6/2014 | Yamagata | | G01N 35/00 53/287 |
| 2015/0273468 A1 * | 10/2015 | Croquette | | B01L 3/50825 422/63 |
| 2017/0350878 A1 * | 12/2017 | Holmes | | G01N 33/50 |

FOREIGN PATENT DOCUMENTS

| | | |
|---|---|---|
| EP | 1882949 | 1/2008 |
| EP | 2385015 | 11/2011 |
| JP | 2010 100312 | 5/2010 |
| WO | WO 03/034038 | 4/2003 |

OTHER PUBLICATIONS

Written Opinion of the International Searching Authority, PCT/EP2013/066365, dated Feb. 21, 2014.
Danish Search Report, Patent No. 15067985, dated Mar. 12, 2013.

* cited by examiner

TEST TUBE CAPPING AND DE-CAPPING APPARATUS

This application is the U.S. National Stage of International Application No. PCT/EP2013/066365, filed on Aug. 5, 2013, published in English, which claims priority under 35 U.S.C. § 119 or 365 to Denmark Application No. PA 2012 00492, filed Aug. 7, 2012.

FIELD

The present invention relates to a capping and de-capping device and a method for attaching and removing caps from tubes, and, more particularly, a device and method for removing screw-threaded caps from test tubes such as micro tubes used in laboratories or micro-biological systems.

BACKGROUND

High value biological samples are often stored and processed using so-called SBS format racks containing a plurality of test tubes. Such racks may contain, for example, 96 test tubes in an array of 8 by 12 apertures designed to hold the tubes securely. The test tubes and their contents may be maneuvered in a processing system, for example between a cold store and various processing stations and may be required to be filled (partly or fully) or processed simultaneously or individually.

Conventionally, capping and de-capping has either been carried out by hand or else by means of a capping and de-capping unit one test tube at a time, either while they are still held in the rack or after they have been separated from the rack. This is not only tedious (particularly in the case of manual capping and de-capping), but also slow as it is usual for multiple tubes to require processing in the same way at the same time.

It is known to provide a linear array of capping and de-capping units to allow for the capping and de-capping of a row of tubes, but such systems have been bulky as a result of the dimensions of the drive mechanisms for the capping and de-capping units, the close spacing of the test tubes requiring the drive mechanisms of the capping and de-capping units to be remote from the capping and de-capping heads and disposed over a larger footprint than the rack because of their size.

EP 1882949 disclose a capping and de-capping apparatus having a test tube rack support for supporting a rack containing a plurality of capped test tubes in a given position. A head unit supports a two-dimensional array of capping and de-capping spindles, each of which includes a clutch and a capping and de-capping spigot or socket, the spindles being aligned with the test tube positions defined in the rack. A drive mechanism moves the tubes and the head unit relatively towards and away from one another in use, when a rack containing capped test tubes is disposed in the rack support, causing engagement and disengagement of the spigots or sockets with and from the tube caps. A spindle drive system provides simultaneous rotation of the spigots or sockets together after engagement with the caps, either to attach caps to the tubes or detach caps from the tubes. Ejection of the caps from the spigots is caused by moving an external net in the opposite direction to the spindle translational movement thereby detaching all sockets from all caps in one movement.

SUMMARY

On this background the present applicants realized the need for a simple and customizable apparatus for capping and de-capping one or more test tubes held within the tight confinement of standard laboratory test tube racks; which will permit each tube to be individually capped and de-capped for some laboratory uses while retaining the ability to cap or de-cap all tubes within the rack at the same time for other uses.

This object is achieved by providing a apparatus for capping and de-capping test tubes having one or more capping and de-capping grippers equipped with a capping and de-capping socket unit wherein said one or more grippers each are configured with an ejector pin moveably arranged within said one or more grippers and wherein said ejector pin may perform a translational movement relative to the said one or more grippers effecting the release from the socket unit of a cap retained by the socket unit.

This object is further achieved by providing a capping and de-capping gripper equipped with a capping and de-capping socket unit said gripper and socket unit so arranged as to permit said ejector pin to perform a translational movement relative to the said gripper and socket unit effecting the release from the socket unit of a cap retained by the socket unit.

This object is further achieved by providing said ejector pin with an actuator unit capable of rotating said ejector pin.

This object is further achieved by providing said capping and de-capping socket unit with a socket for grabbing and retaining a test tube cap adaptable to a plurality of different laboratory test tube systems.

This object is further achieved by combining the above apparatus with a programmable logic controller, microprocessor, or computer application, either internal or external to said apparatus, for controlling the movement of the gripper units and ejector pins individually, in subgroups of the total array of gripper units and ejector pins, or the totality of the gripper units and ejector pins and by providing a user interface permitting the user to select which gripper or grippers within the array of grippers that shall engage a corresponding tube within the rack.

Further objects, features, advantages, and properties of the apparatus and method according to the present disclosure will become apparent from the detailed description.

BRIEF DESCRIPTION OF THE DRAWINGS

In the following detailed portion of the present description, the teachings of the present document will be explained in more detail with reference to the exemplary embodiments shown in the drawings, in which:

In Figure 1a the combination of the apparatus according to the present invention with an external control unit is exemplarily shown without this embodiment being thereby considered preferred.

DETAILED DESCRIPTION

In the following detailed description the capping and de-capping apparatus, the capping and de-capping gripper, the capping and de-capping socket unit and the application for controlling the capping and de-capping grippers individually are described in detail with reference to the exemplary embodiments.

Figure 1A:
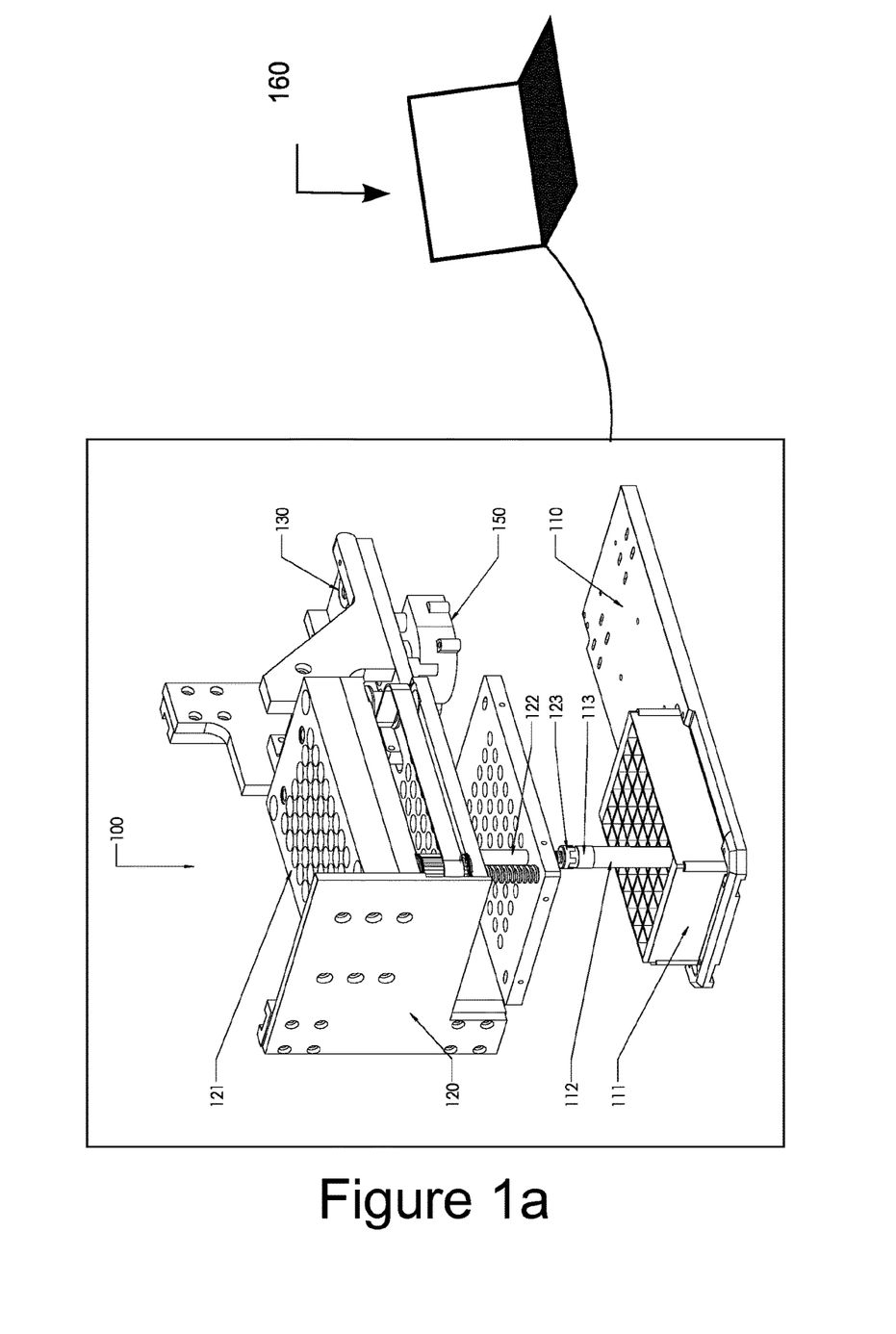
FIG. 1a and 1b present two different views of the capping and de-capping apparatus according to the teachings herein.
Figure 1B:
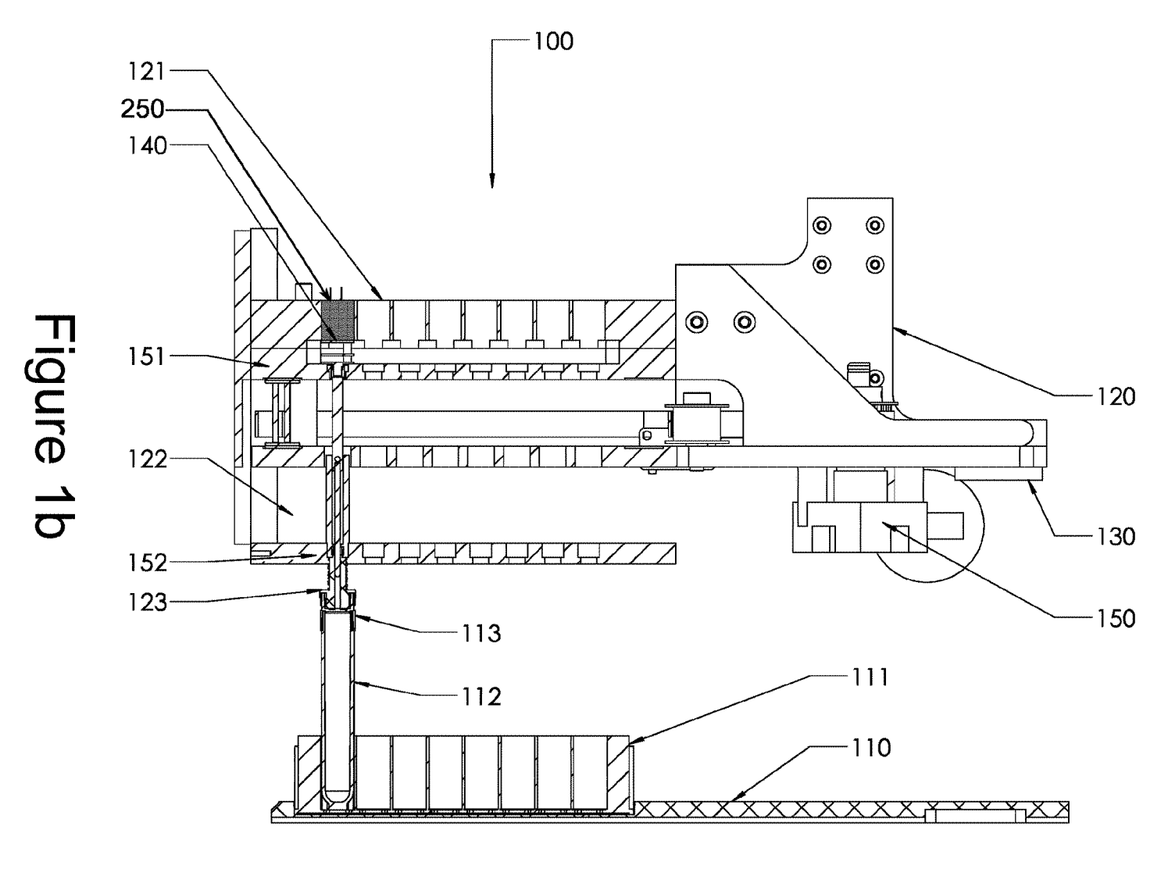

An embodiment of the capping and de-capping apparatus 100 according to the invention is depicted in detail in FIG. 1a and 1b. In FIG. 1a an external control unit 160 is shown for illustrative purposes. As is clear to the skilled person, the control unit 160 with user interface can be external to the apparatus 100 for some purposes or can be integrated into the apparatus for other purposes. Further the connection between the control unit 160 and the apparatus 100 may be a cable as shown in the figure or could be a WIFI-signal or other like options depending on the skilled person's choice, such choices being considered trivial in a modern laboratory setting.

The capping and de-capping apparatus 100 is equipped with a rack support 110 for supporting a tube rack 111, preferably a test tube rack, for containing in at least one given position within the rack 111 at least one tube 112, preferably a test tube, fitted to receive and/or dispose of a cap 113, preferably a screw cap.

The capping and de-capping apparatus 100 is further equipped with a head unit 120 supporting a two-dimensional array 121 (in the present exemplary embodiment a 6 * 8 array) of capping and de-capping grippers 122, each capping and de-capping gripper 122 including a capping and de-capping socket unit 123 capable of engaging and retaining a cap, the capping and de-capping grippers 122 being aligned with the tube positions within the rack 111.

The capping and de-capping apparatus 100 is also equipped with a drive system 130 for moving the rack support 110 and head unit 120 relatively towards and away from one another in use, when a rack 111 containing at least one tube 112 is disposed in the rack support 110, to cause engagement and disengagement of at least one capping and de-capping socket unit 123 with and from the at least one tube 112.

The capping and de-capping apparatus 100 is further equipped with a drive system 140 for rotating at least one capping and de-capping gripper 122 and the capping and de-capping socket unit 123 attached thereto, said rotation of the capping and de-capping socket unit 123, after engagement of the at least one capping and de-capping socket unit 123 with at least one cap 113, can cause either attachment of the at least one cap 113 to the at least one tube 112 within the rack 111 when the at least one capping and de-capping gripper 122 rotate in the one direction or detachment of the at least one cap 113 from the at least one tube 112 when the at least one capping and de-capping gripper 122 rotate in the other direction.

Further, the capping and de-capping apparatus 100 is further equipped with a drive system 150 internal to the head unit 120, permitting a first attachment body 151 and a second attachment body 152 to perform a movement towards and away from each other independently of the movement of the head unit 120 when moved by the drive system 150.

Finally, the capping and de-capping apparatus 100 is further equipped with a control unit 160, said control unit being preferably a programmable logic controller, a microprocessor, or a computer application, said control unit 160 being either internal or external to said apparatus 100, for controlling the movement, both translational and rotational, of the gripper units and ejector pins individually, in subgroups of the total array of gripper units and ejector pins, or the totality of the gripper units and ejector pins and by providing a user interface permitting the user to select which gripper or grippers within the array of grippers that shall engage a corresponding tube within the rack. In a preferred embodiment the control unit 160 is equipped with means for measuring the torque associated with each rotating gripper, preferably by measuring the current supplied to the drive system 140 needed to effectuate a continued rotation of at least one gripper, and means for terminating the rotation of the at least one gripper if a given threshold value is exceeded.

Figure 2:
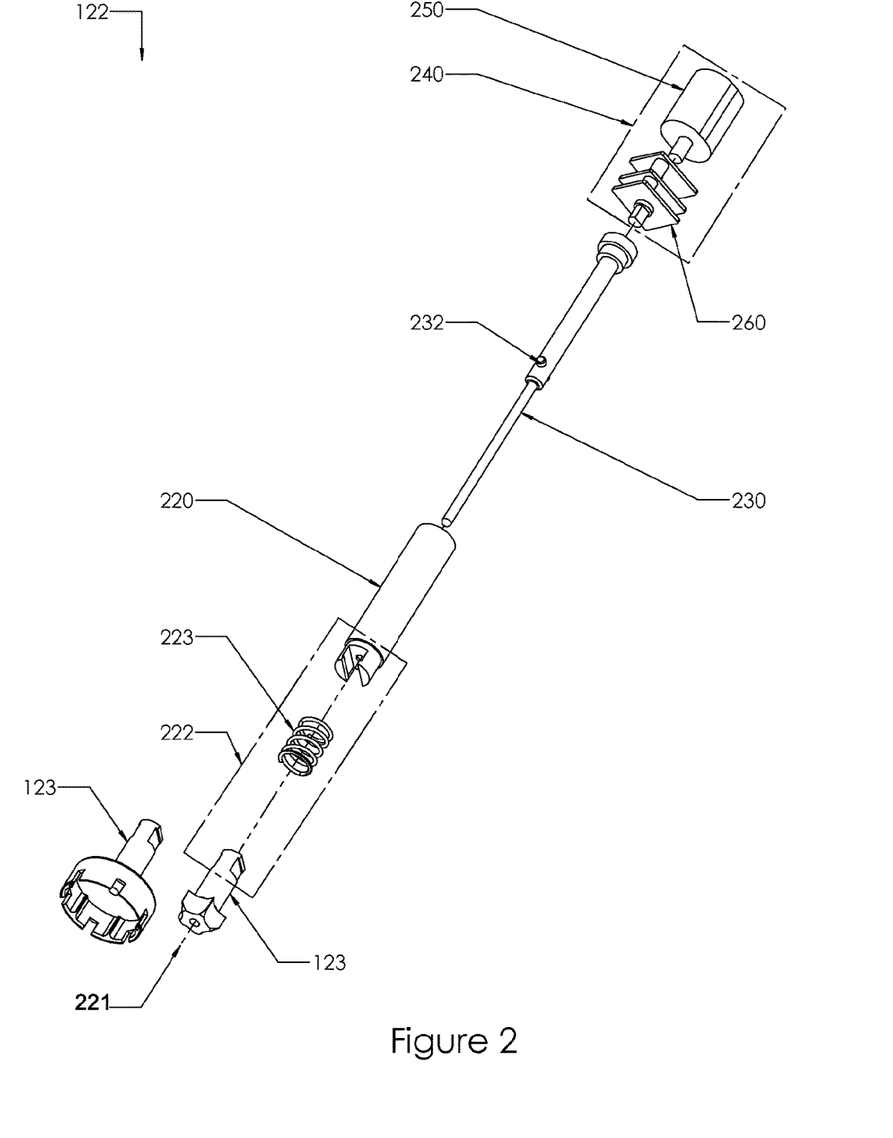
FIG. 2 is a view of a capping and de-capping gripper according to the teachings herein.

An embodiment of the capping and de-capping gripper 122 according to the invention is depicted in detail in FIG. 2.

The capping and de-capping gripper 122 comprises a capping and de-capping socket unit 123 capable of engaging and retaining a cap, said capping and de-capping socket unit 123 having a through going passage 211, an ejector pin guide 220 also having a through going passage 221, and an ejector pin 230, and wherein the socket unit 123 and the ejector pin guide 220 are so arranged to permit said ejector pin 230 to perform a translational movement within said socket unit 123 and said ejector pin guide 220.

The ejector pin 230 is stationary with respect to the above mentioned first attachment body 151, for example because it is attached to said first attachment body 151. Likewise the ejector pin guide 220 is stationary with respect to said second attachment body 152, for example because it is attached to said second attachment body 152. Accordingly, upon the activation of the drive system 150, said translational movement of said ejector pin 230 within said socket unit 123 and said ejector pin guide 220 can be effectuated.

While it is possible for said capping and de-capping socket unit 123 and said ejector pin guide to be manufactured in one piece, it is preferred that they are not. Therefore in a preferred embodiment the capping and de-capping socket unit 123 is attachable and detachable to said ejector pin guide 220 such that when said capping and de-capping socket unit 123 is attached to said ejector pin guide 220, said ejector pin 230 may perform a translational movement within the said ejector pin guide 220 attached to the said capping and de-capping socket unit 123.

The drive system 140 for rotating the ejector pin 230 comprises a plurality of actuator units 240 coupled to said ejector pin 230, each actuator unit 240 comprising an actuator 250, preferably an electro motor, mechanically coupled to said ejector pin 230. In a preferred embodiment of the actuator unit 240, said actuator 250 is mechanically coupled to said ejector pin 230 by means of a gear 260. Additionally the drive system 140 may comprise internal or external means for sensing the torque on said ejector pin 230, e.g. if the actuator 250 is an electro motor, by detecting a change in the current supplied to the actuator 250, and internal or external means for halting the actuator movement if a certain threshold torque is exceeded. Preferably, however, the means for sensing torque and the means for halting the actuator movement are associated with the control unit 160.

In this further embodiment wherein said ejector pin 230 is rotated by said actuator unit 240, preferably in the configuration of an actuator 250 coupled to a gear 260, said ejector pin 230 includes means for transferring the rotational movement created by said actuator unit 240 to said ejector pin guide 220 or said capping and de-capping socket unit 123. In one embodiment said means for transferring the rotational movement of said ejector pin 230 to said ejector pin guide 220 consists in a pin 232 protruding from said ejector pin 230 at a right angle and into a longitudinal groove in the ejector pin guide 220.

In a further embodiment the ejector pin guide 220 further comprises means 222 for attaching a capping and de-capping socket unit 123 to said ejector pin guide 220. In a preferred embodiment the means 222 for attaching a capping and de-capping socket unit 123 further comprises a biasing means 223, preferably a coil spring.

Figure 3A:
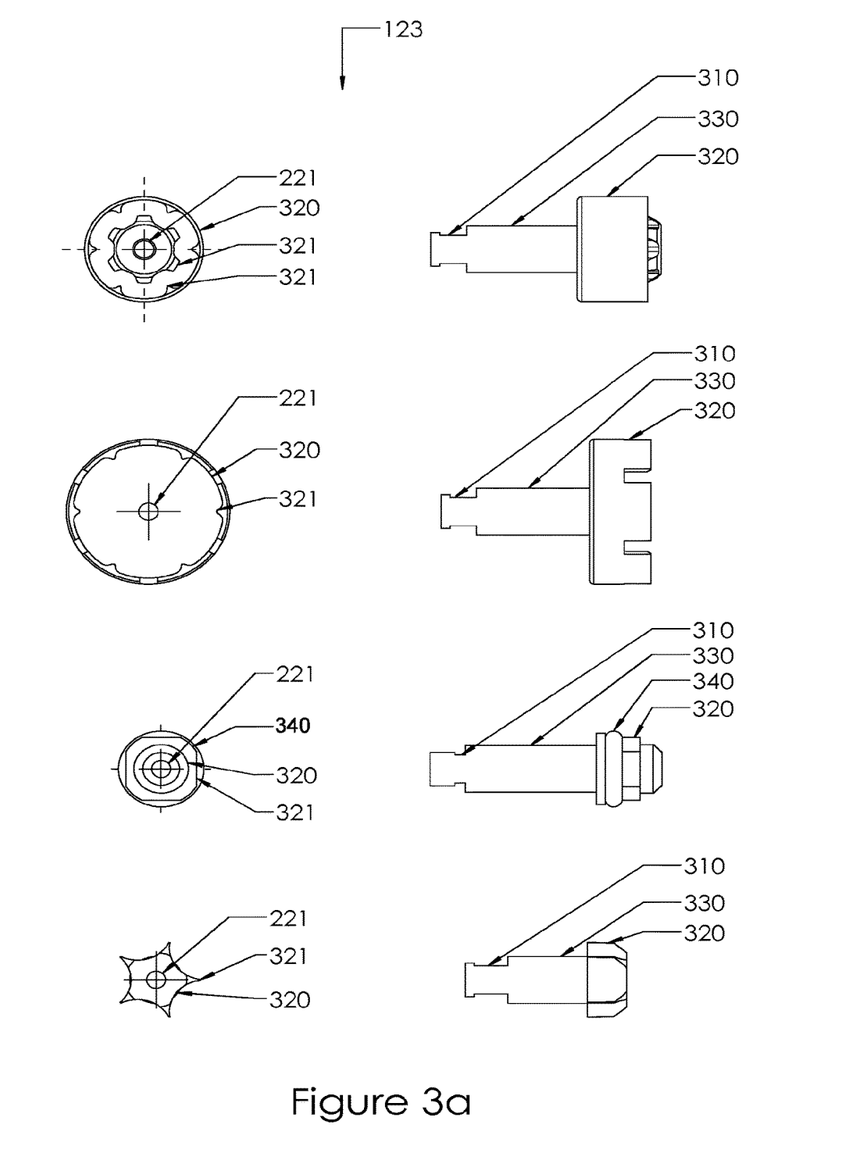
FIG. 3a is an exemplary view of four of the capping and de-capping socket units according to the teachings herein.
Figure 3B:
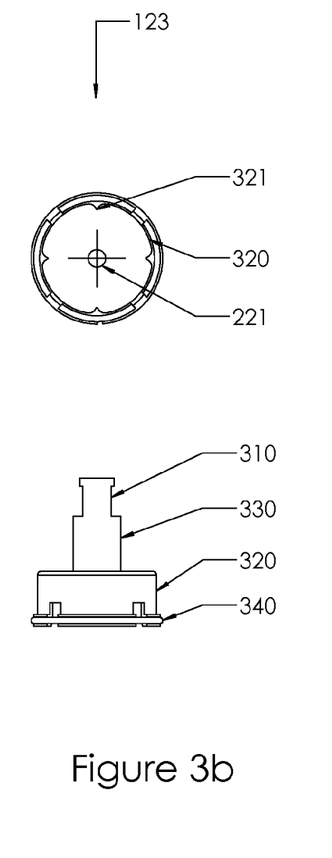
FIG. 3b is an exemplary view of a capping and de-capping socket unit combined with an external spring encircling the capping and de-capping socket.

An embodiment of the capping and de-capping socket unit 123 according to the invention is depicted in detail in FIG. 3.

A capping and de-capping socket unit 123 capable of engaging and retaining a cap 113, preferably a test tube cap, for use with a capping and de-capping gripper 122 having a gripper connector 310 for attaching and detaching to said capping and de-capping gripper 122, or in the most preferred embodiment, to said ejection pin guide 220, is described in FIG. 3. The less preferred embodiment of a capping and de-capping socket unit permanently attached to said ejection pin guide is not shown in the figure. It is however to be understood, and such is also clear from the contents of FIG. 3, that the socket unit 123 is so conceived that the manner of which it engages and disengages a cap is independent of how it attaches to the ejector pin guide 220, and whether this attachment is permanent or not.

Both in the embodiment of a socket unit 213 permanently attached to said ejector pin guide 220 or in the preferred embodiment of a socket unit 123 which is attachable and detachable to said ejector pin guide 220, said socket unit 123 comprises a socket 320 for connecting to a cap, preferably a test tube cap, and even more preferably a screw cap for a test tube. In the preferred embodiment of an attachable or detachable socket unit 123, the socket unit 123 may further comprise a mechanical connection 330 between said gripper connector 310 and said socket 320, said gripper connector 310, said socket 320 and said optional mechanical connection 330 each having a through going passage 221.

The socket unit 123 and ejector pin guide 220 are preferably manufactured from a plastics material, preferably in a molding process such as injection molding. When the socket unit is permanently attached to said ejector pin guide 220, also this assembly may be manufactured from a plastics material, preferably in a molding process such as injection molding. When the socket unit 123 is not permanently attached to said ejector pin guide 220, said ejector pin guide 220 may also be manufactured from a material different from plastics, including metals such as but not limited to, aluminum or stainless steel, and using other means for manufacturing of said ejector pin guide 220 than injection molding.

Known plastics materials which are useful in the manufacture of the socket unit 123 and ejector pin guide 220 can be PEEK (Polyetheretherketone) or POM (Polyoximethylene) but also other plastics materials will be known to the skilled person.

The socket 320 is described in further detail in FIGS. 3a and b. A variety of test tube caps are known in the art and it is a further aim of the present invention to enable the attachment of the socket unit 123 in a simple manner to the test tube caps by applying a simple and adaptable method of attachment.

To this purpose each socket 320 is equipped with at least one friction pin 321, but preferably with a plurality of friction pins 321. A socket 320 according to the invention further has a through going passage 221, to permit the passage of the said ejector pin 230 through the said socket 320.

A socket 320 according to the present invention is so manufactured that upon engagement with a test tube cap 113, the socket 320 is squeezed over the test tube cap 113 and/or, where the test tube cap 113 contains a grove for inserting a socket into said grove, the socket 320 may further be inserted into said grove. Independently of the method of attachment for use with a specific test tube cap, the at least one friction pin 321 ensures a tight contact between the socket 320 and the test tube cap 113 such that when the capping and de-capping gripper 122 is undergoing a movement, either a translation or a translation combined with a rotation, the cap 113 is retained within the socket 320 until ejected using the ejector pin 230.

In one embodiment of the socket 320, for use with a test tube cap 113 that does not have a grove into which a socket can be inserted, the socket 320 has an inner geometrical shape that matches the outer geometrical shape of the test tube cap 113, that it is about to engage with the at least one, but preferably a plurality of friction pins 321 arranged on the inner surface of the socket, such that the pins protrude towards the center of the ejector pin guide 220.

In another embodiment of the socket 320, for use with a cap 113 that does have a grove into which a socket can be inserted, the socket 320 has at least one, but preferably a plurality of friction pins 321 arranged on the surface of said socket 320 facing away from the said ejector pin guide 220.

In a further embodiment, for use with some test tube caps, it is preferable to combine the two previous modes of arranging the at least one friction pin 321.

In FIGS. 3a and 3b an improvement of the socket unit 123 is shown which offers enhanced attachment to a test tube cap 113, this being particularly useful when said cap is damaged or worn, wherein a spring 340 is placed externally to the socket 320, encircling said socket, thereby providing either an internal friction force on a cap, when mounted internally (FIG. 3a) or a compression force (FIG. 3b) towards the center of the socket 320 and thus increasing the friction on said cap 113 exerted by the at least one friction pin 321. The shape of the spring is determined by shape of the socket 320 to which it is external. The spring 340 may be made from any elastic material, but preferentially it is made from an elastomer, such as (but not limited to) rubber or PVC, preferentially in the form of an O-ring, or circlips such as e.g. a metallic spring ring.

In operation, the head unit 120 is moved towards the rack support 110 by the drive system 130. A capping and de-capping gripper 122 engages an opposing cap 113 on an opposing test tube 112 via the socket 320 on the socket unit 123. Disengagement of the cap 113 from the test tube 112 is brought about by the concerted movement of the drive system 130 moving now the head unit 120 away from the rack support 110 and a rotational movement of the actuator unit 240 connected to said capping and de-capping gripper 122 in contact with said cap 113. Caps in contact with a capping and de-capping gripper 122 but not undergoing a rotation by the actuator unit 240 forming part of such a capping and de-capping gripper 122 are not removed from their respective test tubes 112.

To attach a removed cap, the above procedure is reversed. It is stopped when the means for sensing the torque on the ejector pin registers that a certain threshold torque is exceeded. The tube 112 now having a cap has its cap ejected from the socket 320, by moving said tube 112 towards the ejector pin 230 by the drive mechanism 150, whereby the socket unit 123 and ejector pin guide 220 are moved past that end of the ejector pin 230 that is in contact with the cap 113 and said cap is thereby released, freeing the capping and de-capping system 100 to perform a new cycle of capping and de-capping.

The term "comprising" as used in the claims does not exclude other elements or steps. The term "a" or "an" as used in the claims does not exclude a plurality. The controller may fulfill the functions of several means recited in the claims. The reference signs used in the claims shall not be construed as limiting the scope.

Although the present invention has been described in detail for purpose of illustration, it is understood that such detail is solely for that purpose, and variations can be made therein by those skilled in the art without departing from the scope of the invention.

The invention claimed is:

1. A capping and de-capping apparatus for capping and de-capping capable tubes disposed in a rack with a two dimensional array of apertures for holding said tubes, said apparatus comprising:
    a rack support for supporting said rack,
    a head unit supporting a two-dimensional array of capping and de-capping grippers, each capping and de-capping gripper including a capping and de-capping socket unit configured to engage and retain a cap, said capping and de-capping grippers being aligned with tube apertures defined by the array in said rack,
    a drive mechanism configured to move the rack support and head unit relatively towards and away from one another, to cause engagement or disengagement of capping and de-capping socket units with or from caps of tubes; and
    a drive system configured to rotate capping and de-capping grippers and the capping and de-capping socket units attached thereto, wherein rotation of the capping and de-capping socket units, after engagement of capping and de-capping socket units with caps, causes attachment of the caps to the tubes within the rack when the capping and de-capping grippers rotate in one direction and causes detachment of the caps from the tubes when the capping and de-capping grippers rotate in the opposite direction; and wherein
    each capping and de-capping gripper has a throughgoing passage extending through the capping and de-capping gripper and the capping and de-capping socket unit attached thereto,
    an ejector pin is moveably arranged within said throughgoing passage;
    and wherein said ejector pin is configured to perform a translational movement relative to the at least one capping and de-capping gripper and capping and de-capping socket unit attached to said gripper, thereby contacting the cap retained in the socket unit to eject the cap from the socket unit, effecting a release of a cap retained within the capping and de-capping socket unit; and
    the drive system includes an actuator attached to each ejector pin at an end of the capping and de-capping gripper opposite to the socket unit to impart rotary motion to each ejector pin about its longitudinal axis, the ejector pin imparting rotational movement to the capping and de-capping socket unit attached to said gripper
    wherein the capping and de-capping gripper comprises an ejector pin guide also having a throughgoing passage,
    wherein said socket unit and said ejector pin guide are so aligned that when said socket unit is attached to said guide, said ejector pin can perform the translational movement within the said guide and said socket unit;
    the ejector pin transferring the rotational movement through said ejector pin guide or to said capping and de-capping socket unit.

2. A capping and de-capping apparatus according to claim 1 wherein each capping and de-capping gripper has an individual actuator configured such that each tube received in said rack can be capped and/or de-capped independently.

3. A capping and de-capping apparatus according to claim 1, wherein said apparatus further comprises a control unit configured to control the operation of each of said capping and de-capping grippers and each of said ejector pins independently from one another.

4. A capping and de-capping apparatus according to claim 3 wherein each capping and de-capping gripper is individually rotationally actuated and controlled.

5. A capping and de-capping apparatus according to claim 3 further comprising a user interface associated with said control unit and configured to permit a user to decide which capping and de-capping grippers shall attach and/or detach selected caps to selected tubes in the two-dimensional array of apertures.

6. A capping and de-capping apparatus according to claim 1 wherein said caps are screw caps, and said tubes are laboratory test tubes.

7. A capping and de-capping gripper comprising:
    a capping and de-capping socket unit having a throughgoing passage and capable of engaging and retaining a cap,
    an ejector pin guide also having a throughgoing passage, and
    an ejector pin;
        wherein said socket unit and said ejector pin guide are so aligned that when said socket unit is attached to said guide, said ejector pin can perform a translational movement within said guide and said socket unit, causing the ejector pin to contact the cap retained in the socket unit to eject the cap from the socket unit;
        said capping and de-capping gripper further comprising an actuator unit configured to induce a rotational movement in said ejector pin upon actuation,
        said actuator unit comprising an actuator,
        said actuator unit attached to said ejector pin, at an end of the capping and de-capping gripper opposite to the socket unit, and
        the rotational movement of said ejector pin being transferred to said ejector pin guide or to said capping and de-capping socket unit;
        wherein said capping and de-capping socket unit comprises
            a gripper connector detachably connecting to the ejector pin guide to rotate with the ejector pin guide,
            a capping and de-capping socket, and
            a mechanical connection between said gripper connector and said capping and de-capping socket;
        each of said gripper connector, said capping and de-capping socket, and said mechanical connection having a throughgoing passage; and wherein when the gripper connector, the capping and de-capping socket, and the mechanical connection are assembled to form said capping and de-capping socket unit, the throughgoing passages are so aligned that when said capping and de-capping socket unit is attached to said guide, said ejector pin can perform a translational movement within the said guide and said capping and de-capping socket unit;

said capping and de-capping socket having an external spring encircling said capping and de-capping socket.

8. A capping and de-capping gripper according to claim 7 wherein said socket unit is attachable and detachable to be rotated by said ejector pin guide to which rotational movement of said ejector pin is transferred.

9. A capping and de-capping gripper according to claim 7 further comprising a control unit configured to detect a torque on said actuator unit and to halt the rotational movement of said actuator unit if a predetermined threshold value of torque acting on said actuator unit is exceeded.

10. A capping and de-capping gripper according to claim 7 wherein said capping and de-capping socket further comprises a biasing means external to said mechanical connection.

11. A capping and de-capping gripper according to claim 7 wherein said capping and de-capping socket further comprises at least one friction pin oriented towards, away, or both towards and away, at right angles from the center line of said throughgoing passage, and wherein the said at least one friction pin is oriented to either grab around a cap or to be inserted into a cavity within said cap or both.

12. A capping and de-capping gripper according to claim 7 wherein said capping and de-capping socket unit or said capping and de-capping socket is made from plastic.

13. A capping and de-capping gripper according to claim 12, said capping and de-capping socket unit or capping and de-capping socket having been injection molded.

14. A method of operating a capping and de-capping apparatus using the capping and de-capping apparatus of claim 1, to attach or detach at least one cap, said method comprising:

moving the head unit towards the rack support by the drive mechanism, engaging the capping and de-capping gripper carried by said head unit to the opposing cap on the opposing test tube placed in the rack on said rack support via a socket on the socket unit, detaching the cap from the test tube by concerted movement of the head unit away from the rack support and the simultaneous rotational movement of at least one gripper unit caused by at least one actuator unit connected to at least one of the ejector pins to translate rotary motion to said at least one capping and de-capping gripper in contact with said cap, whereby caps, in contact with the capping and de-capping grippers that are not undergoing a rotation by their respective actuator units, are not detached from their respective test tubes;

attaching the removed cap by reversing the above steps and stopping when a sensed torque on the ejector pin exceeds a certain threshold torque; and to eject the tube now having the cap, moving said tube and ejector pin toward each other by the drive mechanism, whereby the socket unit and the ejector pin guide are moved past an end of the ejector pin in contact with the cap thereby releasing said tube, freeing the capping and de-capping apparatus to perform a new cycle of capping and de-capping.

15. A capping and de-capping gripper according to claim 7 wherein the external spring is an O-ring manufactured from an elastomeric material.

* * * * *